(12) United States Patent
Campbell

(10) Patent No.: US 11,749,084 B1
(45) Date of Patent: Sep. 5, 2023

(54) HOSPITAL BED ALERT DEVICE

(71) Applicant: Melinda Campbell, St Albans, NY (US)

(72) Inventor: Melinda Campbell, St Albans, NY (US)

(*) Notice: Subject to any disclaimer, the term of this patent is extended or adjusted under 35 U.S.C. 154(b) by 42 days.

(21) Appl. No.: 17/533,181

(22) Filed: Nov. 23, 2021

(51) Int. Cl.
| | |
|---|---|
| G08B 21/00 | (2006.01) |
| G08B 23/00 | (2006.01) |
| G08B 21/22 | (2006.01) |
| A61B 5/00 | (2006.01) |
| A61G 7/018 | (2006.01) |
| A61G 7/05 | (2006.01) |
| A61B 5/11 | (2006.01) |

(52) U.S. Cl.
CPC ............ G08B 21/00 (2013.01); G08B 23/00 (2013.01); *A61B 5/1115* (2013.01); *A61B 5/6891* (2013.01); *A61G 7/018* (2013.01); *A61G 7/05* (2013.01); *G08B 21/22* (2013.01)

(58) Field of Classification Search
CPC .. A61B 5/00; A61B 5/11; A61B 5/112; A61B 5/1115; A61B 5/1128; G01H 40/67; G01H 50/20; G06F 19/00; G06Q 10/00; G06Q 30/00; G06Q 30/02; G08B 21/00; G08B 23/00; G08B 7/06
See application file for complete search history.

(56) References Cited

U.S. PATENT DOCUMENTS

| | | | |
|---|---|---|---|
| 5,349,340 A | 9/1994 | Blumenthal | |
| 5,418,696 A | 5/1995 | Izzo, Sr. | |
| 6,508,580 B2 | 1/2003 | Collins | |
| 8,134,463 B2 | 3/2012 | Black | |
| 8,493,194 B1 | 7/2013 | Sholman | |
| 2008/0015903 A1* | 1/2008 | Rodgers | G06Q 30/02 705/3 |
| 2009/0211026 A1 | 8/2009 | Schoff | |
| 2018/0078180 A1* | 3/2018 | Allen | A61B 5/1117 |
| 2021/0007676 A1* | 1/2021 | Chronis | A61B 5/1115 |

OTHER PUBLICATIONS

NPL Search (Feb. 26, 2023).*

* cited by examiner

*Primary Examiner* — Van T Trieu
(74) *Attorney, Agent, or Firm* — Kyle A. Fletcher, Esq.

(57) ABSTRACT

The hospital bed alert device comprises a control circuit and a gurney. The control circuit mounts in the gurney. The control circuit generates an alarm selected form a plurality of alarms while the gurney is in motion. The plurality of alarms comprises a first alarm and a second alarm. The first alarm is used for situation that is not life-threatening. The second alarm is used for situations that are life threatening. The first alarm generates and first audible alarm and a first visual alarm. The second alarm generates a second audible alarm and a second visual alarm. The second audible alarm is audibly distinct from the first audible alarm. The second visual alarm is visually distinct from the first visual alarm.

14 Claims, 4 Drawing Sheets

HOSPITAL BED ALERT DEVICE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of signaling systems involving audio and visual signals. (G08B7/06)

SUMMARY OF INVENTION

The hospital bed alert device comprises a control circuit and a gurney. The control circuit mounts in the gurney. The control circuit generates an alarm selected form a plurality of alarms while the gurney is in motion. The plurality of alarms comprises a first alarm and a second alarm. The first alarm is used for situation that is not life-threatening. The second alarm is used for situations that are life threatening. The first alarm generates and first audible alarm and a first visual alarm. The second alarm generates a second audible alarm and a second visual alarm. The second audible alarm is audibly distinct from the first audible alarm. The second visual alarm is visually distinct from the first visual alarm.

These together with additional objects, features and advantages of the hospital bed alert device will be readily apparent to those of ordinary skill in the art upon reading the following detailed description of the presently preferred, but nonetheless illustrative, embodiments when taken in conjunction with the accompanying drawings.

In this respect, before explaining the current embodiments of the hospital bed alert device in detail, it is to be understood that the hospital bed alert device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the hospital bed alert device.

It is therefore important that the claims be regarded as including such equivalent construction insofar as they do not depart from the spirit and scope of the hospital bed alert device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 2:
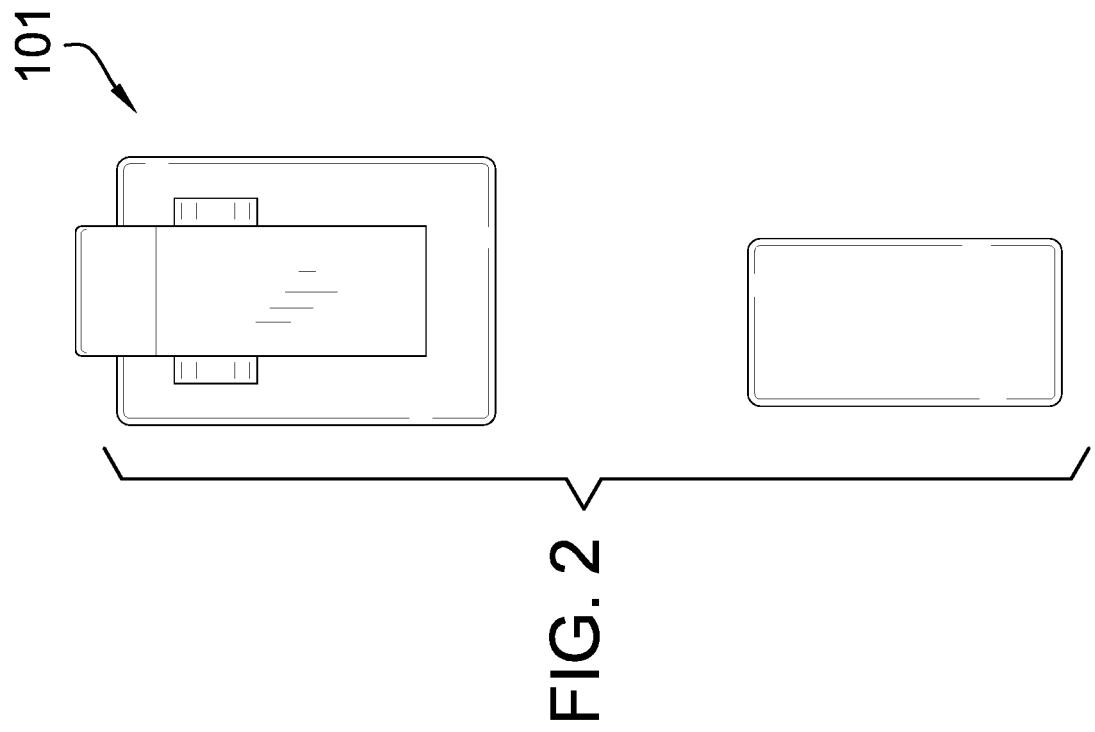
FIG. 2 is a rear view of an embodiment of the disclosure.
Figure 1:
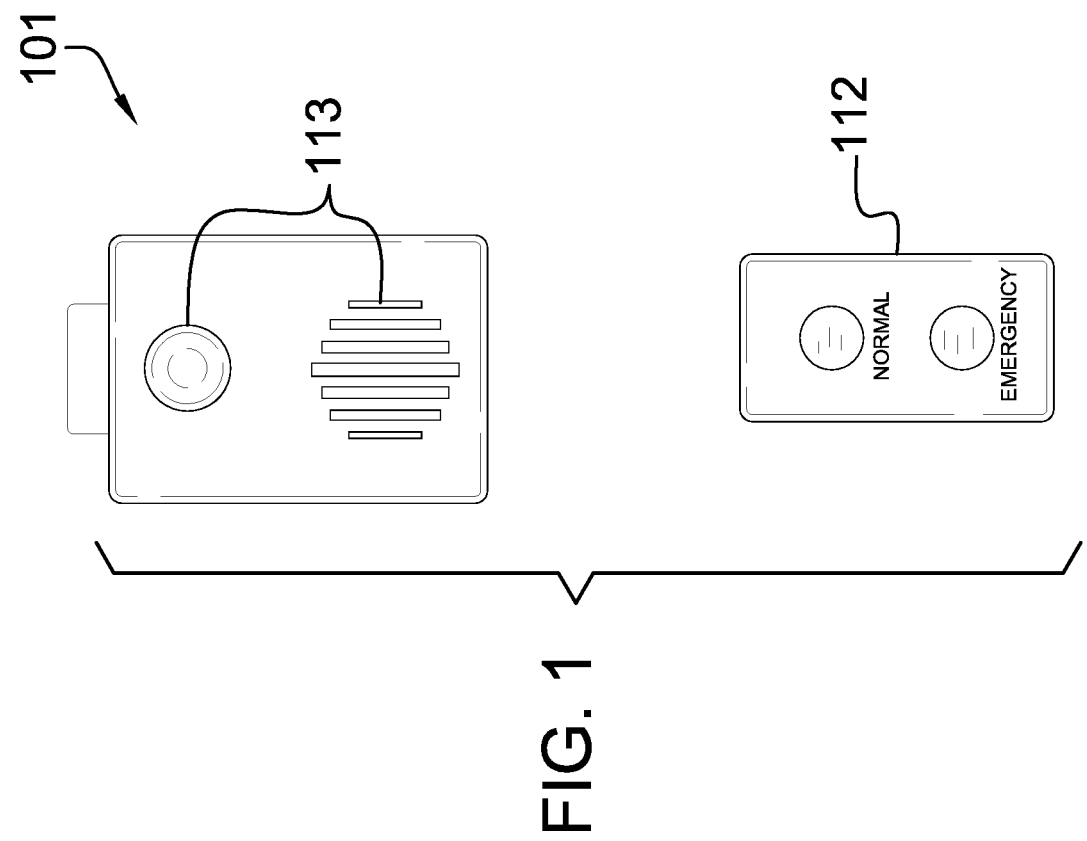
FIG. 1 is a front view of an embodiment of the disclosure.
Figure 4:
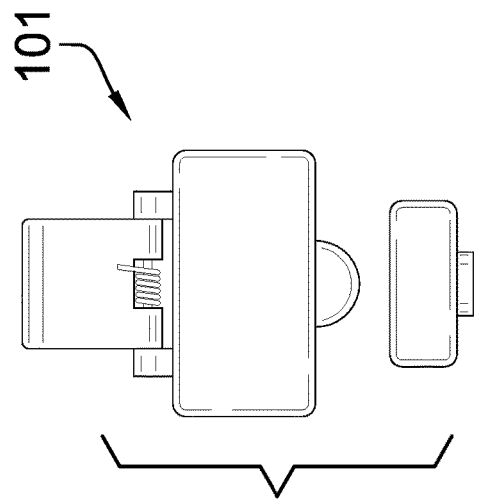
FIG. 4 is a top view of an embodiment of the disclosure.
Figure 5:
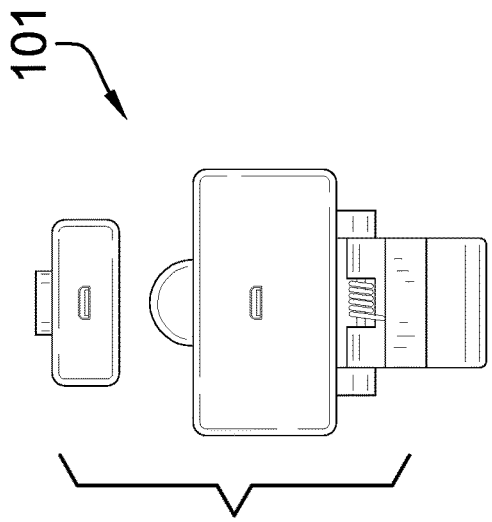
FIG. 5 is a bottom view of an embodiment of the disclosure.
Figure 3:
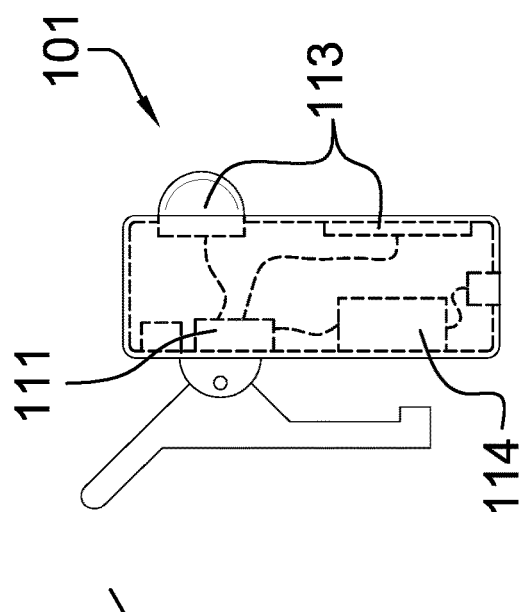
FIG. 3 is a side view of an embodiment of the disclosure.
Figure 3:
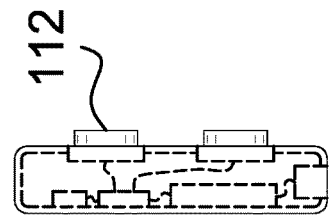
Figure 6:
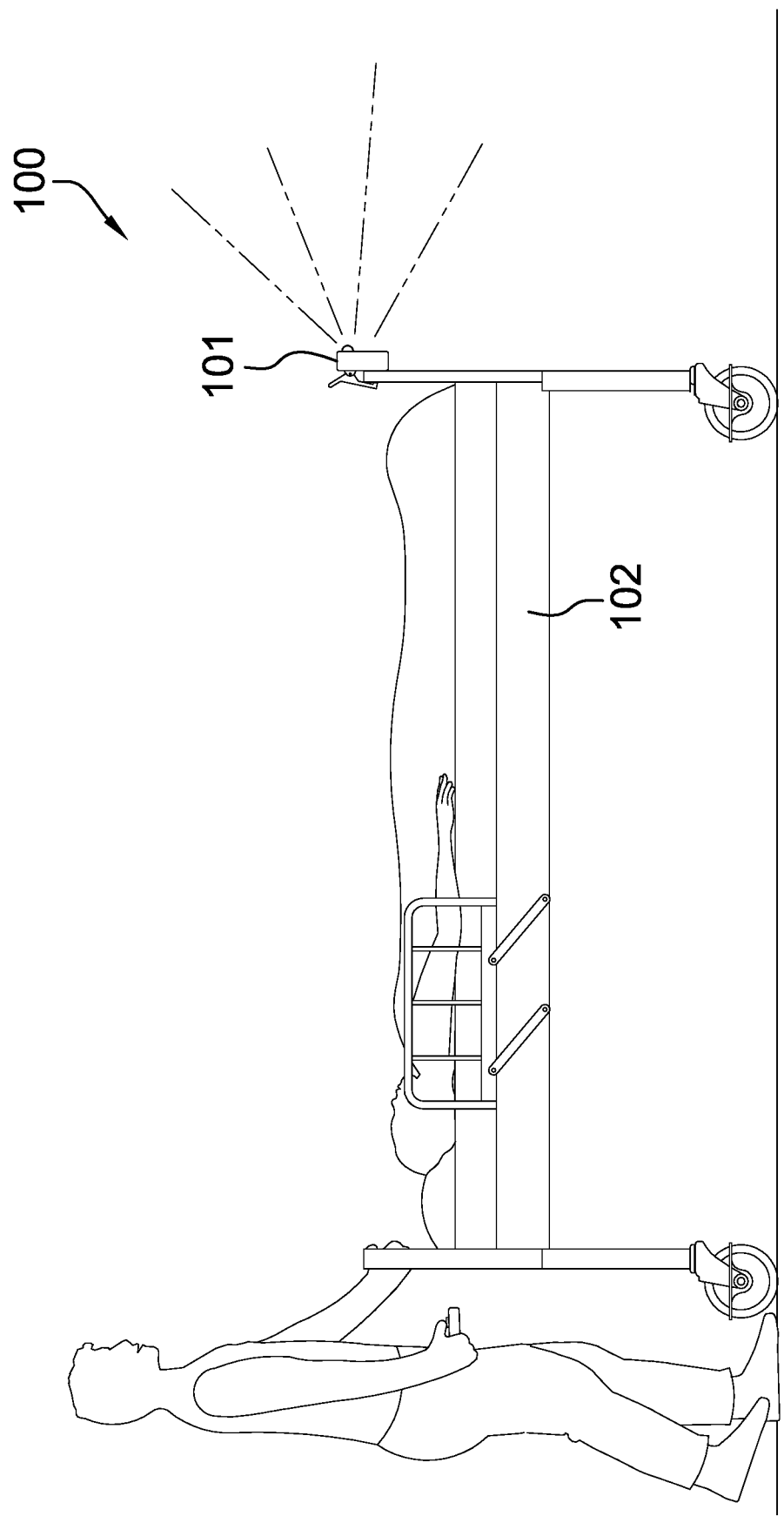
FIG. 6 is an in-use view of an embodiment of the disclosure.
Figure 7:
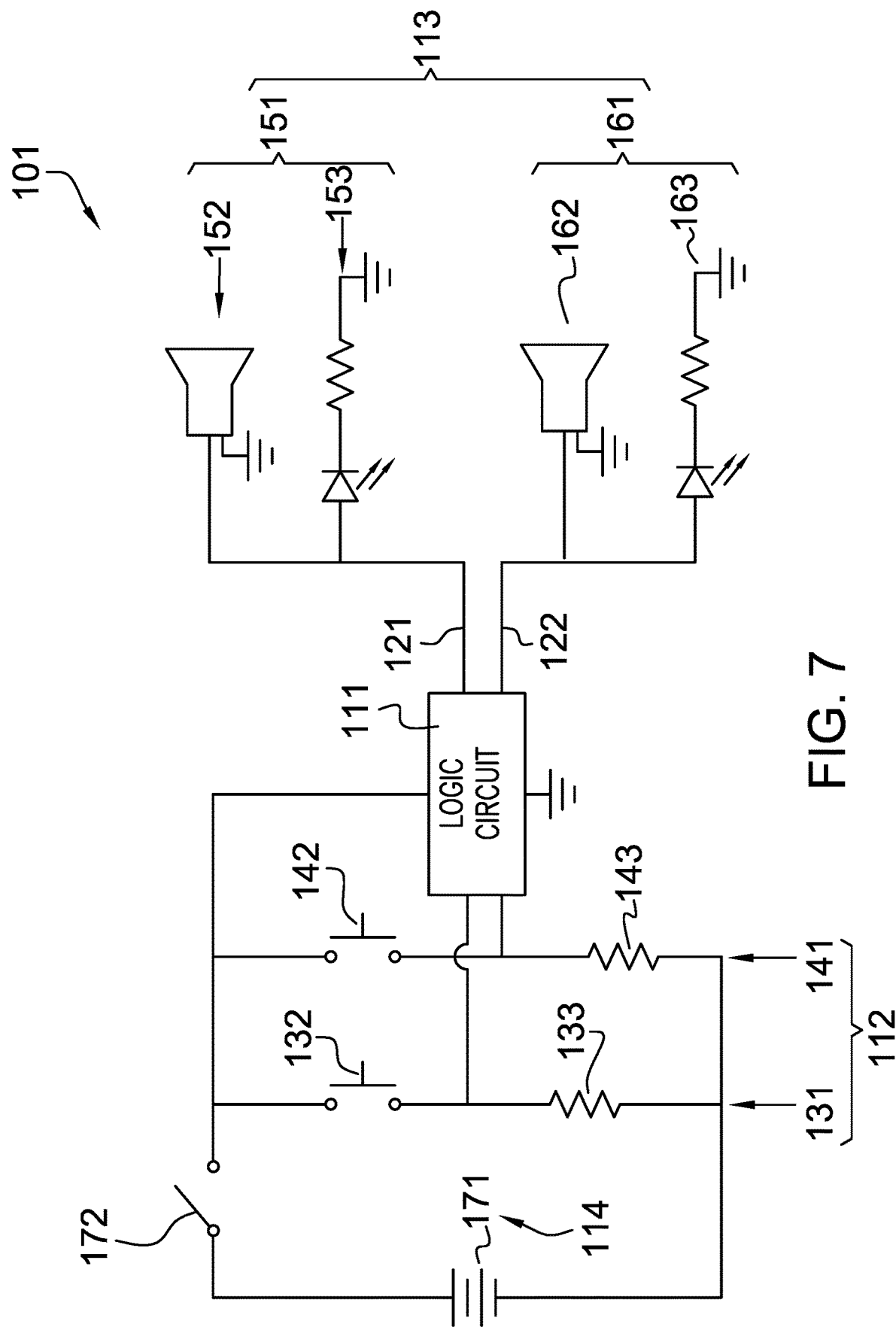
FIG. 7 is a schematic view of an embodiment of the disclosure.

Detailed reference will now be made to one or more potential embodiments of the disclosure, which are illustrated in FIGS. 1 through 7.

The hospital bed alert device 100 (hereinafter invention) comprises a control circuit 101 and a gurney 102. The control circuit 101 mounts on the gurney 102. The control circuit 101 generates an alarm selected form a plurality of alarms while the gurney 102 is in motion. The plurality of alarms comprises a first alarm and a second alarm. The first alarm is used for situation that is not life-threatening. The second alarm is used for situations that are life threatening. The first alarm generates and first audible alarm and a first visual alarm. The second alarm generates a second audible alarm and a second visual alarm. The second audible alarm is audibly distinct from the first audible alarm. The second visual alarm is visually distinct from the first visual alarm. The gurney 102 is a bed that is used to transport a patient. The gurney 102 is defined elsewhere in this disclosure.

The control circuit 101 is an electric circuit. The control circuit 101 generates a first audible alarm that indicates that the gurney 102 is moving in a situation that is not life-threatening. The control circuit 101 generates a first visible alarm that indicates that the gurney 102 is moving in a situation that is not life-threatening. The control circuit 101 generates a second audible alarm that indicates that the gurney 102 is moving in a situation that is life-threatening. The control circuit 101 generates a second visible alarm that indicates that the gurney 102 is moving in a situation that is life-threatening. The control circuit 101 comprises a logic circuit 111, a plurality of selection circuits 112, a plurality of alarm circuits 113, and a power circuit 114. The logic circuit 111, the plurality of selection circuits 112, the plurality of alarm circuits 113, and the power circuit 114 are electrically interconnected.

The logic circuit 111 is an electric circuit. The logic circuit 111 electrically connects to the power circuit 114. The logic circuit 111 electrically connects to the plurality of selection circuits 112. The logic circuit 111 monitors the operation of the plurality of selection circuits 112. The logic circuit 111 electrically connects to the plurality of alarm circuits 113. The logic circuit 111 electrically controls the operation of the plurality of alarm circuits 113.

The logic circuit 111 further comprises a first alarm signal 121 and a second alarm signal 122. The first alarm signal 121 is an electric signal generated by the logic circuit 111. The first alarm signal 121 electrically connects to an alarm circuit selected from the plurality of alarm circuits 113. The logic circuit 111 initiates the first alarm signal 121 to actuate the audible and visual indications associated with the first alarm. The second alarm signal 122 is an electric signal generated by the logic circuit 111. The second alarm signal 122 electrically connects to an alarm circuit selected from the plurality of alarm circuits 113. The logic circuit 111 initiates the second alarm signal 122 to actuate the audible and visual indications associated with the second alarm.

Each selection circuit selected from the plurality of selection circuits 112 is an electric circuit. Each selection circuit selected from the plurality of selection circuits 112 electrically connects to the logic circuit 111. Each selection circuit selected from the plurality of selection circuits 112 forms an interface that transmits an electric signal to the logic circuit 111. The signal transmitted by each selection circuit selected from the plurality of selection circuits 112 indicates to the logic circuit 111 that an action should be taken. The indicated action is selected from the group consisting of: a) initiating the first alarm; and, b) initiating the second alarm. The plurality of selection circuits 112 comprises a first selection circuit 131 and a second selection circuit 141.

The first selection circuit 131 is an electric circuit. The first selection circuit 131 is a manually operated structure. The first selection circuit 131 electrically connects to the logic circuit 111. The first selection circuit 131 forms an interface that transmits an electric signal to the logic circuit 111 indicating that the logic circuit 111 should initiate the first alarm. The first selection circuit 131 further comprises a first momentary switch 132 and a first load resistor 133.

The first momentary switch 132 is a momentary switch. The momentary switch is defined elsewhere in this disclosure. The first momentary switch 132 forms an electric connection between the power circuit 114 and the first load resistor 133. The first momentary switch 132 controls the flow of electric energy from the power circuit 114 into the first load resistor 133. The first load resistor 133 is a resistor. The resistor is defined elsewhere in this disclosure. The logic circuit 111 monitors the first selection circuit 131 by measuring the voltage across the first load resistor 133. The logic circuit 111 uses the measured voltage across the first load resistor 133 as the indication that the logic circuit 111 should initiate the first alarm.

The second selection circuit 141 is an electric circuit. The second selection circuit 141 is a manually operated structure. The second selection circuit 141 electrically connects to the logic circuit 111. The second selection circuit 141 forms an interface that transmits an electric signal to the logic circuit 111 indicating that the logic circuit 111 should initiate the second alarm. The second selection circuit 141 further comprises a second momentary switch 142 and a second load resistor 143.

The second momentary switch 142 is a momentary switch. The momentary switch is defined elsewhere in this disclosure. The second momentary switch 142 forms an electric connection between the power circuit 114 and the second load resistor 143. The second momentary switch 142 controls the flow of electric energy from the power circuit 114 into the second load resistor 143.

The second load resistor 143 is a resistor. The resistor is defined elsewhere in this disclosure. The logic circuit 111 monitors the second selection circuit 141 by measuring the voltage across the second load resistor 143. The logic circuit 111 uses the measured voltage across the second load resistor 143 as the indication that the logic circuit 111 should initiate the second alarm.

Each alarm circuit selected from the plurality of alarm circuits 113 is an electric circuit. Each alarm circuit selected from the plurality of alarm circuits 113 electrically connects to the logic circuit 111. Each alarm circuit selected from the plurality of alarm circuits 113 generates an audible alarm selected from the group consisting of: a) an audible alarm initiating the first alarm has been initiated; and, b) an audible alarm indicating that the second alarm has been initiated. Each alarm circuit selected from the plurality of alarm circuits 113 generates a visible alarm selected from the group consisting of: a) a visible alarm initiating the first alarm has been initiated; and, b) a visible alarm indicating that the second alarm has been initiated.

The logic circuit 111 initiates the actuation of the first audible alarm. The logic circuit 111 initiates the actuation of the second audible alarm. The logic circuit 111 initiates the actuation of the first visible alarm. The logic circuit 111 initiates the actuation of the second visible alarm.

The plurality of alarm circuits 113 further comprises a first alarm circuit 151 and a second alarm circuit 161.

The first alarm circuit 151 is an electric circuit. The first alarm circuit 151 electrically connects to the first alarm signal 121 of the logic circuit 111. The logic circuit 111 controls the operation of the first alarm circuit 151 using the first alarm signal 121. The transmittal of the first alarm signal 121 to the first alarm circuit 151 initiates the announcement of the first audible alarm of the first alarm. The transmittal of the first alarm signal 121 to the first alarm circuit 151 initiates the illumination of the first visible alarm of the first alarm. The first alarm circuit 151 further comprises a first speaker 152 and a first strobe light 153.

The first speaker 152 is a transducer that converts electric energy into an audible sound. The first speaker 152 physically generates the first audible alarm of the first alarm. The logic circuit 111 controls the operation of the first speaker 152. In the first potential embodiment of the disclosure, the first speaker 152 is a buzzer. The first strobe light 153 is a strobe light. The strobe light is defined elsewhere in this disclosure. The logic circuit 111 controls the operation of the first strobe light 153.

The second alarm circuit 161 is an electric circuit. The second alarm circuit 161 electrically connects to the second alarm signal 122 of the logic circuit 111. The logic circuit 111 controls the operation of the second alarm circuit 161 using the second alarm signal 122. The transmittal of the second alarm signal 122 to the second alarm circuit 161 initiates the announcement of the second audible alarm of the second alarm. The transmittal of the second alarm signal 122 to the second alarm circuit 161 initiates the illumination of the second visible alarm of the second alarm. The second alarm circuit 161 further comprises a second speaker 162 and a second strobe light 163.

The second speaker 162 is a transducer that converts electric energy into an audible sound. The second speaker 162 physically generates the first audible alarm of the first alarm. The logic circuit 111 controls the operation of the second speaker 162. In the first potential embodiment of the disclosure, the second speaker 162 is a buzzer. The second strobe light 163 is a strobe light. The strobe light is defined elsewhere in this disclosure. The logic circuit 111 controls the operation of the second strobe light 163.

The audible sound generated by the second speaker 162 is audibly distinct from the audible sound generated by the first speaker 152. The visual illumination generated by the second strobe light 163 is visually distinct from the visual illumination generated by the first strobe light 153.

The power circuit 114 is an electric circuit. The power circuit 114 provides the electric energy necessary to power the operation of the logic circuit 111. The power circuit 114 provides the electric energy necessary to power the operation of the plurality of selection circuits 112. The power circuit 114 provides the electric energy necessary to power the operation of the plurality of alarm circuits 113. The power circuit 114 comprises an external power source 171 and a master switch 172.

The external power source 171 is an externally provides source of electric energy. In the first potential embodiment of the disclosure, the external power source 171 is a battery. The master switch 172 is a maintained electric switch. The master switch 172 controls the flow of electric energy from the power circuit 114 to the logic circuit 111. The master switch 172 controls the flow of electric energy from the power circuit 114 to the plurality of selection circuits 112. The external power source 171 controls the flow of electric energy from the power circuit 114 to the plurality of alarm circuits 113. The master switch 172 is the "power switch" of the invention 100.

The following definitions were used in this disclosure:

Battery: As used in this disclosure, a battery is a chemical device consisting of one or more cells, in which chemical energy is converted into electricity and used as a source of power. Batteries are commonly defined with a positive terminal and a negative terminal.

Bed: As used in this disclosure, a bed refers to a structure, typically a furniture item, used for sleeping or resting. When the structure is a furniture item, the bed comprises a frame and a mattress. The frame is a pedestal that elevates the mattress. A bed often further comprises one or more box frames. The one or more box frames are mechanical structures that form secondary pedestals that elevate the mattress above the frame.

Buzzer: As used in this disclosure, a buzzer is two lead electrical device that generates an audible sound when voltage is applied to the two leads.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Exterior: As used in this disclosure, the exterior is used as a relational term that implies that an object is not contained within the boundary of a structure or a space.

External Power Source: As used in this disclosure, an external power source is a source of the energy that is externally provided to enable the operation of the present disclosure. Examples of external power sources include, but are not limited to, electrical power sources and compressed air sources.

Force of Gravity: As used in this disclosure, the force of gravity refers to a vector that indicates the direction of the pull of gravity on an object at or near the surface of the earth.

Gurney: As used in this disclosure, a gurney is a bed that is formed with a pedestal that: a) allows the bed to roll over a supporting surface; and, b) that allows the elevation of the mattress of the bed to be adjusted.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Inferior: As used in this disclosure, the term inferior refers to a directional reference that is parallel to and in the same direction as the force of gravity when an object is positioned or used normally.

Interface: As used in this disclosure, an interface is a physical or virtual boundary that separates two different systems and across which information is exchanged.

Interior: As used in this disclosure, the interior is used as a relational term that implies that an object is contained within the boundary of a structure or a space.

Limit Resistor: As used in this disclosure, a limit resistor is an electrical resistor that is used to limit the flow of electric current through an electrical circuit.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Load Resistor: As used in this disclosure, a load resistor is an electrical resistor that is used to present a voltage to an electrical device. The presented voltage is controlled by controlling the amount of electrical current passing through the load resistor.

Logic Circuit: As used in this disclosure, a logic circuit is electrical device that receives one or more digital or analog inputs and uses those digital or analog inputs to generate one or more digital or analog outputs. This disclosure allows, but does not assume, that the logic circuit is programmable.

Maintained Switch: As used in this disclosure, a maintained switch is a switch that maintains the position that was set in the most recent switch actuation. A maintained switch works in an opposite manner to a momentary switch.

Mattress: As used in this disclosure, a mattress is a disk-shaped structure that forms a cushion used by a patient when lying flat. The superior congruent end of the disk structure of the mattress forms a horizontally oriented surface.

Momentary Switch: As used in this disclosure, a momentary switch is a biased switch in the sense that the momentary switch has a baseline position that only changes when the momentary switch is actuated (for example when a pushbutton switch is pushed or a relay coil is energized). The momentary switch then returns to the baseline position once the actuation is completed. This baseline position is called the "normal" position. For example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

Pedestal: As used in this disclosure, a pedestal is an intermediary load bearing structure that forms a load path between a supporting surface and an object, structure, or load.

Resistance: As used in this disclosure, resistance refers to the opposition provided by an electrical circuit (or circuit element) to the electrical current created by a DC voltage is presented across the electrical circuit (or circuit element). The term impedance is often used for resistance when referring to an AC voltage that is presented across the electrical circuit (or circuit element).

Resistor: As used in this disclosure, a resistor is a well-known and commonly available electrical device that presents a resistance that inhibits the flow of electricity through an electric circuit. Within an electric circuit processing alternating currents, the resistor will not affect the phase of the alternating current. A current flowing through a resistor will create a voltage across the terminals of the resistor.

Roll: As used in this disclosure, the term roll refers to the rotation of an object around an axis or center of rotation. The term roll is often used in the context of the motion of an object that is facilitated by the rotation of one or more wheels or casters.

Speaker: As used in this disclosure, a speaker is an electrical transducer that converts an electrical signal into an audible sound.

Strobe Light: As used in this disclosure, a strobe light is a device that is used to generate flashes of light at regular intervals. The strobe light is often referred to as a strobe.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load of the object is transferred. This disclosure assumes that an object placed on the supporting surface is in an orientation that is appropriate for the normal or anticipated use of the object.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Transducer: As used in this disclosure, a transducer is a device that converts a physical quantity, such as pressure or brightness into an electrical signal or a device that converts an electrical signal into a physical quantity.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A hospital bed alert device comprising
a control circuit and a gurney;
wherein the control circuit mounts on the gurney;
wherein the gurney is a bed that is adapted to transport a patient;
wherein the control circuit generates an alarm selected form a plurality of alarms;
wherein the plurality of alarms comprises a first alarm and a second alarm;
wherein the first alarm is used for situation that is not life-threatening;
wherein the second alarm is used for situations that are life threatening;
wherein the control circuit comprises a logic circuit, a plurality of selection circuits, a plurality of alarm circuits, and a power circuit;
wherein each of the plurality of selection circuits is a manually-operated structure such that each of the plurality of selection circuits is adapted to be selected by hospital personnel who is pushing the gurney with the patient thereon.

2. The hospital bed alert device according to claim 1
wherein the first alarm generates and first audible alarm and a first visual alarm;
wherein the second alarm generates a second audible alarm and a second visual alarm;
wherein the second audible alarm is audibly distinct from the first audible alarm;
wherein the second visual alarm is visually distinct from the first visual alarm.

3. The hospital bed alert device according to claim 2
wherein the control circuit is an electric circuit;
wherein the control circuit generates the first audible alarm that indicates that the gurney is moving in a situation that is not life-threatening;
wherein the control circuit generates the first visible alarm that indicates that the gurney is moving in a situation that is not life-threatening;
wherein the control circuit generates the second audible alarm that indicates that the gurney is moving in a situation that is life-threatening;
wherein the control circuit generates the second visible alarm that indicates that the gurney is moving in a situation that is life-threatening.

4. The hospital bed alert device according to claim 3
wherein the logic circuit, the plurality of selection circuits, the plurality of alarm circuits, and the power circuit are electrically interconnected.

5. The hospital bed alert device according to claim 4
wherein the logic circuit is an electric circuit;
wherein the logic circuit electrically connects to the power circuit;
wherein the logic circuit electrically connects to the plurality of selection circuits;
wherein the logic circuit monitors the operation of the plurality of selection circuits;
wherein the logic circuit electrically connects to the plurality of alarm circuits;
wherein the logic circuit electrically controls the operation of the plurality of alarm circuits.

6. The hospital bed alert device according to claim 5
wherein each selection circuit selected from the plurality of selection circuits is an electric circuit;
wherein each selection circuit selected from the plurality of selection circuits electrically connects to the logic circuit;
wherein each selection circuit selected from the plurality of selection circuits forms an interface that transmits an electric signal to the logic circuit;
wherein the signal transmitted by each selection circuit selected from the plurality of selection circuits indicates to the logic circuit that an action should be taken;
wherein the indicated action is selected from the group consisting of: a) initiating the first alarm; and, b) initiating the second alarm.

7. The hospital bed alert device according to claim 6
wherein each alarm circuit selected from the plurality of alarm circuits is an electric circuit;
wherein each alarm circuit selected from the plurality of alarm circuits electrically connects to the logic circuit;
wherein each alarm circuit selected from the plurality of alarm circuits generates an audible alarm selected from the group consisting of: a) an audible alarm initiating the first alarm has been initiated; and, b) an audible alarm indicating that the second alarm has been initiated;
wherein each alarm circuit selected from the plurality of alarm circuits generates a visible alarm selected from the group consisting of: a) a visible alarm initiating the first alarm has been initiated; and, b) a visible alarm indicating that the second alarm has been initiated;
wherein the logic circuit initiates the actuation of the first audible alarm;
wherein the logic circuit initiates the actuation of the second audible alarm;
wherein the logic circuit initiates the actuation of the first visible alarm;
wherein the logic circuit initiates the actuation of the second visible alarm.

8. The hospital bed alert device according to claim 7
wherein the power circuit is an electric circuit;
wherein the power circuit provides the electric energy necessary to power the operation of the logic circuit;
wherein the power circuit provides the electric energy necessary to power the operation of the plurality of selection circuits;
wherein the power circuit provides the electric energy necessary to power the operation of the plurality of alarm circuits.

9. The hospital bed alert device according to claim 8
wherein the logic circuit further comprises a first alarm signal and a second alarm signal;
wherein the first alarm signal is an electric signal generated by the logic circuit;
wherein the first alarm signal electrically connects to an alarm circuit selected from the plurality of alarm circuits;
wherein the logic circuit initiates the first alarm signal to actuate the audible and visual indications associated with the first alarm;
wherein the second alarm signal is an electric signal generated by the logic circuit;
wherein the second alarm signal electrically connects to an alarm circuit selected from the plurality of alarm circuits;
wherein the logic circuit initiates the second alarm signal to actuate the audible and visual indications associated with the second alarm.

10. The hospital bed alert device according to claim 9
wherein the plurality of selection circuits comprises a first selection circuit and a second selection circuit;
wherein the first selection circuit is an electric circuit;
wherein the first selection circuit is a manually operated structure;
wherein the first selection circuit electrically connects to the logic circuit;
wherein the first selection circuit forms an interface that transmits an electric signal to the logic circuit indicating that the logic circuit should initiate the first alarm;
wherein the second selection circuit is an electric circuit;
wherein the second selection circuit is a manually operated structure;
wherein the second selection circuit electrically connects to the logic circuit;
wherein the second selection circuit forms an interface that transmits an electric signal to the logic circuit indicating that the logic circuit should initiate the second alarm.

11. The hospital bed alert device according to claim 10
wherein the plurality of alarm circuits further comprises a first alarm circuit and a second alarm circuit;
wherein the first alarm circuit is an electric circuit;
wherein the first alarm circuit electrically connects to the first alarm signal of the logic circuit;
wherein the logic circuit controls the operation of the first alarm circuit using the first alarm signal;
wherein the transmittal of the first alarm signal to the first alarm circuit initiates the announcement of the first audible alarm of the first alarm;
wherein the transmittal of the first alarm signal to the first alarm circuit initiates the illumination of the first visible alarm of the first alarm;
wherein the second alarm circuit is an electric circuit;
wherein the second alarm circuit electrically connects to the second alarm signal of the logic circuit;
wherein the logic circuit controls the operation of the second alarm circuit using the second alarm signal;
wherein the transmittal of the second alarm signal to the second alarm circuit initiates the announcement of the second audible alarm of the second alarm;
wherein the transmittal of the second alarm signal to the second alarm circuit initiates the illumination of the second visible alarm of the second alarm.

12. The hospital bed alert device according to claim 11
wherein the power circuit comprises an external power source and a master switch;

wherein the external power source is an externally provides source of electric energy;
wherein in the first potential embodiment of the disclosure, the external power source is a battery;
wherein the master switch is a maintained electric switch;
wherein the master switch controls the flow of electric energy from the power circuit to the logic circuit;
wherein the master switch controls the flow of electric energy from the power circuit to the plurality of selection circuits;
wherein the external power source controls the flow of electric energy from the power circuit to the plurality of alarm circuits.

13. The hospital bed alert device according to claim 12
wherein the first selection circuit further comprises a first momentary switch and a first load resistor;
wherein the first momentary switch is a momentary switch;
wherein the first momentary switch forms an electric connection between the power circuit and the first load resistor;
wherein the first momentary switch controls the flow of electric energy from the power circuit into the first load resistor;
wherein the first load resistor is a resistor;
wherein the logic circuit monitors the first selection circuit by measuring the voltage across the first load resistor;
wherein the logic circuit uses the measured voltage across the first load resistor as the indication that the logic circuit should initiate the first alarm;
wherein the second selection circuit further comprises a second momentary switch and a second load resistor;
wherein the second momentary switch is a momentary switch;
wherein the second momentary switch forms an electric connection between the power circuit and the second load resistor;
wherein the second momentary switch controls the flow of electric energy from the power circuit into the second load resistor;
wherein the second load resistor is a resistor;
wherein the logic circuit monitors the second selection circuit by measuring the voltage across the second load resistor;
wherein the logic circuit uses the measured voltage across the second load resistor as the indication that the logic circuit should initiate the second alarm.

14. The hospital bed alert device according to claim 13
wherein the first alarm circuit further comprises a first speaker and a first strobe light;
wherein the first speaker is a transducer that converts electric energy into an audible sound;
wherein the first speaker physically generates the first audible alarm of the first alarm;
wherein the logic circuit controls the operation of the first speaker;
wherein in the first potential embodiment of the disclosure, the first speaker is a buzzer;
wherein the first strobe light is a strobe light;
wherein the logic circuit controls the operation of the first strobe light;
wherein the second alarm circuit further comprises a second speaker and a second strobe light;
wherein the second speaker is a transducer that converts electric energy into an audible sound;
wherein the second speaker physically generates the first audible alarm of the first alarm;
wherein the logic circuit controls the operation of the second speaker;
wherein the second strobe light is a strobe light;
wherein the logic circuit controls the operation of the second strobe light;
wherein the audible sound generated by the second speaker is audibly distinct from the audible sound generated by the first speaker;
wherein the visual illumination generated by the second strobe light is visually distinct from the visual illumination generated by the first strobe light.

* * * * *